United States Patent [19]

Karapita

[11] 4,374,581

[45] Feb. 22, 1983

[54] SUPPORT UNIT

[76] Inventor: Alexander D. Karapita, 38 Robinter Dr., Willowdale, Ontario, Canada, M2M 3R2

[21] Appl. No.: 55,526

[22] Filed: Jul. 9, 1979

[51] Int. Cl.³ ............................................ B42F 13/00
[52] U.S. Cl. .................................... 248/337; 248/412
[58] Field of Search .............. 248/333, 336, 337, 338, 248/334, 335, 125, 404, 412, 354 H, 487; 403/15; 211/162

[56] References Cited

U.S. PATENT DOCUMENTS

| 481,814 | 8/1892 | Overholt | 248/333 |
|---|---|---|---|
| 874,836 | 12/1907 | Dodge et al. . | |
| 2,453,855 | 11/1948 | Oliver . | |
| 2,453,855 | 11/1948 | Oliver | 403/15 |
| 2,460,997 | 2/1949 | Myers | 211/162 X |
| 2,616,648 | 11/1952 | Budreck | 248/487 |
| 2,658,777 | 11/1953 | Rauglas | 248/333 X |
| 2,938,699 | 5/1960 | Bellmann | 248/354 H |
| 3,048,360 | 8/1972 | Foley . | |
| 3,191,904 | 6/1965 | Karapita | 248/333 |
| 3,321,090 | 5/1967 | Greenstadt | 211/162 |
| 3,807,574 | 4/1974 | Lanza . | |
| 4,073,456 | 2/1978 | Karapita | 248/337 |

FOREIGN PATENT DOCUMENTS 1365427 5/1964 France .
337584 11/1930 United Kingdom .

Primary Examiner—J. Franklin Foss

[57] ABSTRACT

A vertically adjustable suspension support unit having a vertical cylinder and a brake element slidable in the cylinder. The brake element comprises a pair of collars located coaxially in the cylinder with opposed bevels providing a raceway for spherical bearings, the angle of each bevel being between 35° and 70°, preferably 45°, with respect to a transverse plane of the cylinder normal to its axis. The collars are connected to a grip and are movable towards and away from one another to clamp or release the brake element in the cylinder, the brake element being axially rotatable while clamped.

10 Claims, 6 Drawing Figures

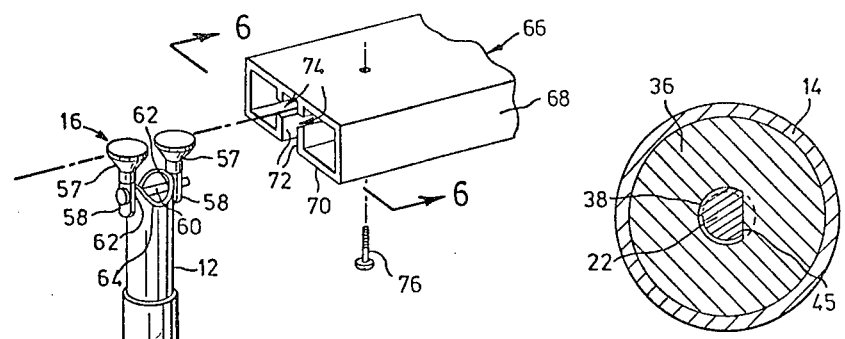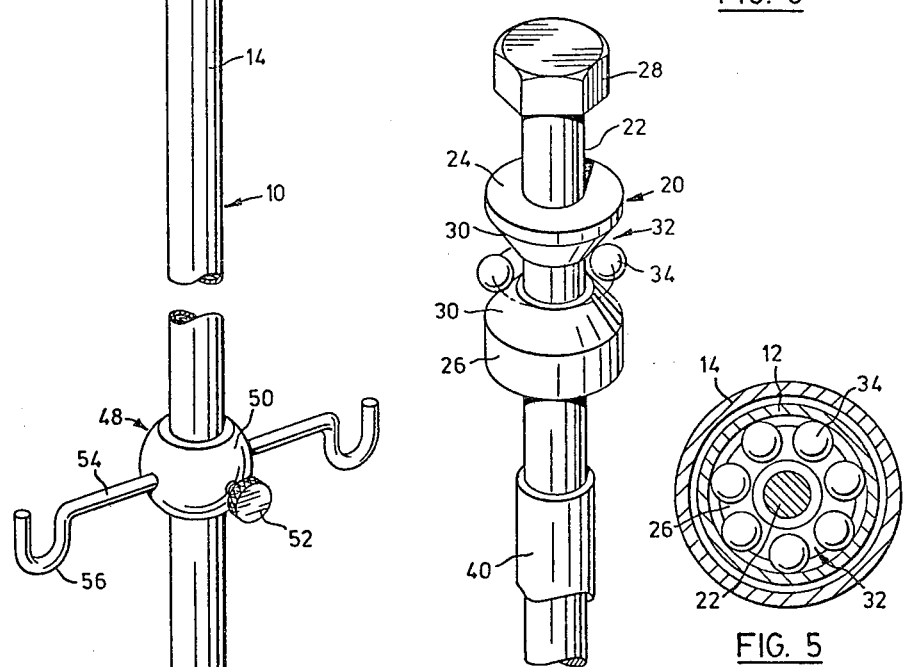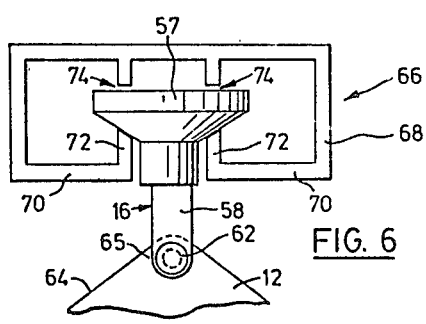

SUPPORT UNIT

FIELD OF THE INVENTION

This invention relates to a vertically adjustable suspension support.

BACKGROUND OF THE INVENTION

Adjustable suspension supports are used for example in hospitals where a support is suspended from the ceiling to carry plasma bottles for intravenous injections. An example of such a support is shown in U.S. Pat. No. 3,191,904 issued June 29, 1965 to A. D. Karapita. The combined weight of a plurality of such bottles makes it difficult to adjust the support rotationally and upwardly, especially when operated by women nurses.

To overcome the problem it has been proposed to use vacuum means with a suspension support and such a device is disclosed in U.S. Pat. No. 4,073,456 issued Feb. 14, 1978 to A. D. Karapita. However, such a support is relatively complex in design and requires a vacuum source.

It is an object of the present invention to provide an improved suspension support which is of simplified construction and relatively simple to operate.

SUMMARY OF THE INVENTION

Essentially the invention consists of a suspension unit comprising a vertical cylinder and means at the upper end of the cylinder for suspension thereof, brake means slidable in the cylinder and having grip means at the lower end thereof, the brake means comprising a pair of spaced collars slidably mounted on a shaft coaxially in the cylinder, the shaft projecting below the cylinder and carrying a grip at the lower end thereof, the shaft being axially rotatable to move the collars selectively towards and away from one another, the collars being bevelled at their outer opposing edges to form a raceway, the angle of the bevelled outer edge of each collar being between 35° and 70° with respect to a transverse plane of the cylinder normal to its axis and the angles being equal, a plurality of spherical bearings being located in the raceway and movable, in moving the collars one towards the other, outwardly to bear against the cylinder and lock the brake means with respect to vertical movement therein, the brake means and the shaft being jointly rotatable about the axis of the shaft, and means connected with the brake means to support an object. The collars being freely slidable on a shaft, stop means on the upper end of the shaft, and a tube concentric with the shaft, the lowermost of the collars bearing against the upper end of the tube and the lower end of the tube bearing against a plug in the lower end of the sleeve, the shaft being freely slidable in the plug through an aperture therein and engaging the grip beneath the plug.

Preferably the angle of the bevelled outer edge of each collar is 45°. Also, the shaft preferably rotates with the object supporting means.

BRIEF DESCRIPTION OF THE DRAWINGS

An example embodiment of the invention is shown in the accompanying drawing in which:

FIG. 1 is a perspective view of a support unit;

FIG. 3 is a cross-section taken along line 3—3 of FIG. 2;

FIG. 4 is a perspective view of the brake means of the unit of FIG. 1;

FIG. 5 is a cross-sectional view taken along line 5—5 of FIG. 2; and

FIG. 6 is an end view of the support bracket taken in the direction of line 6—6 of FIG. 1.

DETAILED DESCRIPTION OF THE INVENTION

Figure 2:
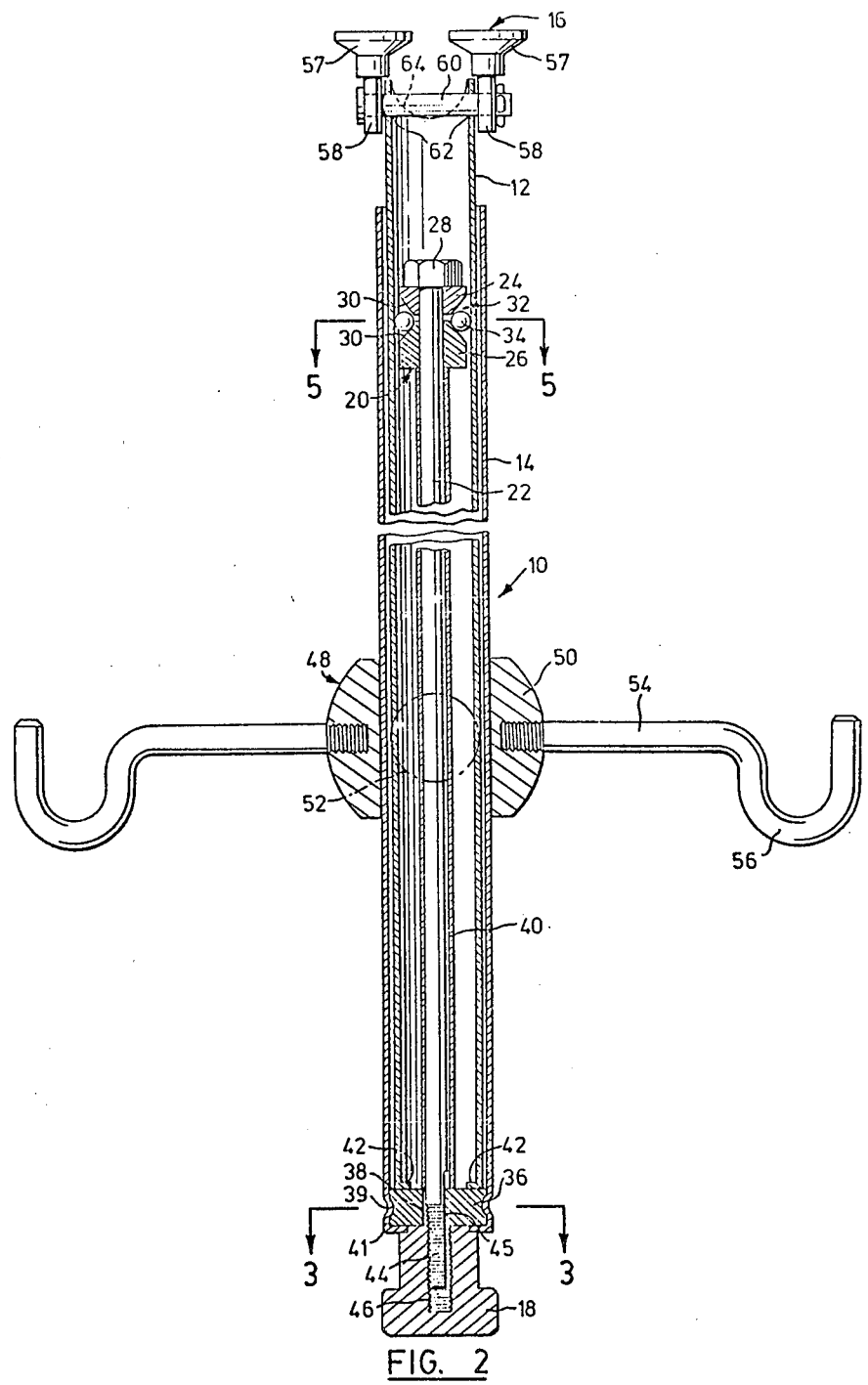
FIG. 2 is a vertical cross-sectional view of the unit of FIG. 1.

The example embodiment consists of a support unit 10 having a pair of vertical telescopic tubes comprising an inner cylinder 12 and an outer sleeve 14 coaxial with the cylinder, a pivot mount 16 carried at the top end of the cylinder, and a grip 18 connected to the bottom end of the sleeve.

A slidable brake element 20 is located within inner cylinder 12 at the upper end of a shaft 22 which is coaxial with the cylinder. Brake element 20 comprises a pair of spaced collars 24, 26 freely slidable along shaft 22 and restrained by a nut 28 from sliding off the upper end of the shaft. The outer edge of each collar 24, 26 has a bevel 30 and the two opposed bevels provide a raceway 32 in which a plurality of spherical bearings 34 are located, as seen especially in FIGS. 4 and 5. The angle of each bevel 30 is between 35° and 70° with respect to a plane normal to the axis of cylinder 12, the angles of the two bevels being equal to provide a vertical chord between the contacting points of the bevels with each bearing 34. An angle less than 35° gives insufficient lateral force against bearings 34 and allows brake element 20 to slip vertically within cylinder 12 while an angle greater than 70° makes the eccentric rotation of the bearings about the vertical chord, and hence horizontal rotation of the braking element, too difficult. The optimum angle of each bevel 30 is 45°, making an included angle of 90° between the two bevels, to perform the combination of functions most efficiently.

The lower end of outer sleeve 14 carries a plug 36 with an axial aperture 38 through which passes shaft 22. Sleeve 14 has a circumferential indent 39 to retain plug 36 and an inwardly turned flange 41 for the same purpose. A tube 40 concentric with shaft 22 spaces brake element 20 from plug 36 and the bottom end of inner cylinder 12 is inturned to provide a flange 42 which prevents the brake element from sliding out from the cylinder.

Shaft 22 has a lower threaded end 44 which is segmented in transverse cross-section to provide an indented face 45. Aperture 38 of plug 36 is similarly segmented, as seen especially in FIG. 3 of the drawings. End 44 of shaft 22 extends freely through aperture 38 and engages a threaded bore 46 in grip 18 which abuts plug 36.

Means to support an object is carried by outer sleeve 14, in the form of a hanger 48 in the example embodiment. Hanger 48 comprises a collar 50 slidably mounted on sleeve 14 and releasably secured on the sleeve by a screw clamp 52. Collar 50 carries a plurality of fixed, outwardly projecting arms 54 each terminating at its free end in a hook 56.

Pivot mount 16 comprises a pair of spaced cups 57 each having a downwardly projecting stem 58. A pivot pin 60 passes transversely through each stem 58 and through opposed aperatures 62 in the upper end of inner cylinder 12 which may have opposed recesses 64 in an axial direction normal to the axis of pin 60 to form trunnions 65 for the pin. Cups 57 are slidable in a ceiling bracket 66 which comprises a frame 68 having a pair inturned flanges 70 forming spaced vertical internal wall members 72 with opposed longitudinal slots 74. Bracket 66 may be fastened to a ceiling by a plurality of screws 76. Cups 57 are received laterally in slots 74 and rest on wall members 72 as seen in FIG. 6 of the drawings.

In the operation of the example embodiment, cylinder 12 and sleeve 14 are locked together by rotating grip 18 in a direction to draw collars 24, 26 together. The segmented portion of shaft 22 interacting with plug 36 prevents sleeve 14 from rotating while grip 18 is being rotated. As collars 24, 26 are drawn together they force bearings 34 radially outwards to bear against the inner wall of cylinder 12 and the friction of the bearings against the cylinder prevents vertical movement of sleeve 14. To lower or raise hanger 48, grip 18 is rotated in the opposite direction which releases the force of bearings 34 acting against the inner wall of cylinder 12, enabling cylinder 12 and sleeve 14 to be moved axially relative to one another.

Unit 10 may be rotated about the axis of cylinder 12 while brake element 20 is locked on the cylinder. This is possible because the included angle of bevels 30 provides bearing points in a vertical chord on each bearing 34, allowing the bearing to rotate eccentrically in a horizontal plane. As mentioned above, an angle of 45° for each bevel (as included angle of 90° between the collars 24, 26) gives an optimum result in this regard. An angle of less than 45° decreases the efficiency of the braking action of the braking element 20 but increases the ease of rotation of the braking element about its axis, while an angle of greater than 45° increases that efficiency but decreases the ease of rotation.

It will be appreciated that outer sleeve 14 is merely a mount for hanger 48 and it could be suitably modified in accordance with the structure of the hanger, for instance it could be shortened if the hanger were to be fixed in the position shown in the drawing. Of course more than one object may be supported by hanger 48 and hooks 56 are provided to hang more than one object, preferably counterbalancing one another.

Unit 10 is suspended from a ceiling by sliding cups 57 into slots 74 of bracket 66 which is fixed to a ceiling, the unit being both slidable along the slots and pivotable transversely on pin 60. If pin 60 is extended in length to locate cups 57 above hooks 56 then greater stability of the objects hung on unit 10 may be achieved.

Collars 24,26 are preferably loosely fitted in cylinder 12 and on shaft 22 to provide adequate braking pressure when brake unit 20 is at the lower end of the cylinder. Also sleeve 14 preferably extends upwardly above brake unit 20, i.e. the upper end of the sleeve is higher than the brake unit, to provide stability when the brake unit is at the lower end of cylinder 12.

The embodiments of the invention in which an exclusive property or privilege is claimed are defined as follows:

1. A suspension support unit comprising:
   a vertical cylinder and means at the upper end of the cylinder for suspension thereof;
   brake means slidable in the cylincder and having grip means at the lower end thereof, the brake means comprising a pair of spaced collars slidably mounted on a shaft coaxially in the cylinder, the shaft projecting below the cylinder and carrying a grip at the lower end thereof, the shaft being axially movable to move the collars selectively towards and away from one another, the collars being bevelled at their outer opposing edges to form a raceway, the angle of the bevelled outer edge of each collar being between 35° and 70° with respect to a transverse plane of the cylinder normal to its axis and the angles being equal, a plurality of spherical bearing being located in the raceway and movable, on moving the collars one towards the other, outwardly to bear against the cylinder and lock the brake means with respect to vertical movement therein with the brake means and the shaft being jointly rotatable about the axis of the shaft; and
   means connected with the brake means to support an object, said support means comprising an outer sleeve concentric with the cylinder, the outer sleeve being slidable on the cylinder and mounted on the grip, and means projecting outwardly from the sleeve to support an object;
   the collars being freely slidable on a shaft, stop means on the upper end of the shaft, and a tube concentric with the shaft, the lowermost of the collars bearing against the upper end of the tube and the lower end of the tube bearing against a plug in the lower end of the sleeve, the shaft being freely slidable in the plug through an aperture therein and engaging the grip beneath the plug.

2. A unit as claimed in claim 1 in which the collars are freely slidable on a shaft, stop means on the upper end of the shaft, and a tube concentric with the shaft, the lowermost of the collars bearing against the upper end of the tube and the lower end of the tube bearing against a plug in the lower end of the sleeve, the shaft being freely slidable in the plug through an aperture therein and engaging the grip beneath the plug.

3. A unit as claimed in claim 1 in which the lower end of the shaft is threaded into the grip, both the lower end portion of the shaft and the aperture in the plug being segmented whereby the shaft is non-rotatable with respect to the sleeve.

4. A unit as claimed in claim 1 or claim 3 in which the lower end of the cylinder terminates in an inturned flange whereby the brake means is stopped from passing out therefrom.

5. A suspension unit as claimed in claim 1 in which the angle of the bevelled outer edge of each collar is 45°.

6. A unit as claimed in claim 1 in which the outwardly projecting means is slidable along the sleeve and releasably clamped thereon.

7. A unit as claimed in claim 1 in which the outwardly projecting means comprises a hanger having a collar slidable on the outer sleeve, and at least one arm projecting outwardly from the collar;
   said clamping means clamping the collar releasably on the sleeve.

8. A unit as claimed in claim 1 in which the support means comprises a transverse pivot pin carried by the cylinder, each end of the pin having means projecting radially therefrom for sliding engagement with a ceiling bracket.

9. A unit as claimed in claim 8 in which that end cylinder adjacent the pin is recessed on each side of the pin to form trunnions therefor.

10. A unit as claimed in claim 1 in which the upper end of the sleeve is higher than the brake means.

* * * * *